(12) United States Patent
Bocirnea

(10) Patent No.: US 8,583,730 B2
(45) Date of Patent: *Nov. 12, 2013

(54) METHOD AND APPARATUS FOR PROVIDING IN-BAND CLIENT TELEMETRY DATA

(71) Applicant: McKesson Financial Holdings, Hamilton (BM)

(72) Inventor: Radu Catalin Bocirnea, New Westminster (CA)

(73) Assignee: McKesson Financial Holdings

( * ) Notice: Subject to any disclaimer, the term of this patent is extended or adjusted under 35 U.S.C. 154(b) by 25 days.

This patent is subject to a terminal disclaimer.

(21) Appl. No.: 13/654,815

(22) Filed: Oct. 18, 2012

(65) Prior Publication Data

US 2013/0046819 A1  Feb. 21, 2013

Related U.S. Application Data

(63) Continuation of application No. 12/781,371, filed on May 17, 2010, now Pat. No. 8,335,821.

(51) Int. Cl.
*G06F 15/16* (2006.01)
(52) U.S. Cl.
USPC ............................ 709/203; 709/224; 709/206

(58) Field of Classification Search
USPC .................. 709/206, 203; 379/106.1, 106.02; 702/183, 184, 188; 600/301
See application file for complete search history.

(56) References Cited

U.S. PATENT DOCUMENTS

| | | | |
|---|---|---|---|
| 7,653,186 B2 * | 1/2010 | Hosain et al. | 379/106.01 |
| 8,065,342 B1 * | 11/2011 | Borg et al. | 707/803 |
| 2004/0103144 A1 | 5/2004 | Sallam et al. | |
| 2005/0157856 A1 | 7/2005 | Humphries | |
| 2005/0251579 A1 | 11/2005 | Ngo et al. | |
| 2007/0287430 A1 * | 12/2007 | Hosain et al. | 455/414.1 |
| 2008/0137823 A1 * | 6/2008 | Abichandani et al. | 379/106.01 |
| 2009/0006840 A1 | 1/2009 | Birger et al. | |
| 2010/0241722 A1 | 9/2010 | Seminaro et al. | |
| 2010/0321204 A1 | 12/2010 | Bae et al. | |
| 2011/0090837 A1 * | 4/2011 | Duchscher et al. | 370/312 |
| 2011/0158210 A1 | 6/2011 | Cemper | |
| 2011/0195701 A1 * | 8/2011 | Cook et al. | 455/422.1 |

* cited by examiner

*Primary Examiner* — Abdullahi Salad
(74) *Attorney, Agent, or Firm* — Alston & Bird LLP

(57) ABSTRACT

A method for providing in-band client telemetry data may include receiving a message, from a first application, intended to be communicated to a second application via a network, the message being otherwise unrelated to client telemetry data. The method may further include inserting client telemetry data collected at a client device executing the first application into a portion of the message and providing for communication of the message to a server device executing the second application. A corresponding computer program product and apparatus are also provided.

16 Claims, 4 Drawing Sheets

METHOD AND APPARATUS FOR PROVIDING IN-BAND CLIENT TELEMETRY DATA

CROSS REFERENCE TO RELATED APPLICATIONS

This application is a continuation of U.S. Appl. No. 12/781,371 filed May 17, 2010, which is hereby incorporated herein in its entirety by reference.

TECHNOLOGICAL FIELD

Embodiments of the present invention relate generally to health care management solutions and, more particularly, relate to the provision of client telemetry data within standard messages.

BACKGROUND

Many aspects of the provision of medical care and the management of many aspects of the healthcare system now involve the use of computers and computer applications. For example, recent efforts have been made to move to electronic medical records (EMR). With clinical documentation systems moving to electronic media, clinical data may be available for incorporation into a number of different applications designed to assist in the management or use of such data. Computerized provider order entry (CPOE) is another example of a development that may improve the ability to electronically access information related to physician's orders. Many other applications are also being developed to utilize electronic information on people and processes to manage the provision of various aspects of patient care including the provision of predictive care.

As the availability of electronic clinical data is increasing, the demand for applications that utilize such data to provide information, guidance and services is also increasing. Many applications have been developed to assist hospitals, clinics, doctors, insurance companies, and other healthcare related service providers with various aspects of improving patient care and organizational management. However, decisions on what applications to employ and even what network infrastructure to adopt can vary widely depending on the needs and resources of each respective organization.

In certain environments, it may be preferable to centralize resources in one or more network servers and employ less robust (thin client) terminals to access the centralized resources. In these and some other architectures, a substantial amount of round trips of communication information between the client and server may be required in order to execute certain applications or communicate certain information. Firewalls, the implementation of network address translation (NAT) and other common network characteristics inherent in the architectures described above may tend to increase network latency. Although it may otherwise be useful at the server end to have information on network performance, status, resource utilization, user behavior and other client related data that may be referred to as "telemetry data", the provision of such information may, in many cases, require yet further communication overhead, which may further increase network latency.

Accordingly, it may be desirable to provide an improved mechanism by which client telemetry data may be acquired in network based communications.

BRIEF SUMMARY

A method, apparatus and computer program product are therefore provided to enable the provision of an in-band client telemetry data in a manner that may address some of the problems discussed above. Accordingly, for example, information on client telemetry data may be provided without increasing the number of messages or the number or round trips that are already in existence in a particular network. In this regard, for example, embodiments of the present invention may enable the piggybacking of client telemetry data onto standard client-server communications.

In one exemplary embodiment, a method for providing in-band client telemetry data is provided. The method may include receiving a message, from a first application, intended to be communicated to a second application via a network, the message being otherwise unrelated to client telemetry data. The method may further include inserting client telemetry data collected at a client device executing the first application into a portion of the message and providing for communication of the message to a server device executing the second application.

In another exemplary embodiment, a computer program product for providing in-band client telemetry data is provided. The computer program product may include at least one computer-readable storage medium having computer-executable program code instructions stored therein. The computer-executable program code instructions may include program code instructions for receiving a message, from a first application, intended to be communicated to a second application via a network, the message being otherwise unrelated to client telemetry data, inserting client telemetry data collected at a client device executing the first application into a portion of the message, and providing for communication of the message to a server device executing the second application.

In another exemplary embodiment, an apparatus for providing in-band client telemetry data is provided. The apparatus may include processing circuitry. The processing circuitry may be configured for receiving a message, from a first application, intended to be communicated to a second application via a network, the message being otherwise unrelated to client telemetry data, inserting client telemetry data collected at a client device executing the first application into a portion of the message and providing for communication of the message to a server device executing the second application.

In one exemplary embodiment, a method for providing in-band client telemetry data is provided. The method may include receiving a message from a client device. The message may include client telemetry data inserted into a portion of the message at the client device. The message may have been intended to be communicated from a first application of the client device to a second application (e.g., of a server device) via a network in association with inter-application communication that is otherwise unrelated to client telemetry data. The method may further include extracting client telemetry data from the message, and enabling reception of the message by the second application with the client telemetry data removed.

In another exemplary embodiment, a computer program product for providing in-band client telemetry data is provided. The computer program product may include at least one computer-readable storage medium having computer-executable program code instructions stored therein. The computer-executable program code instructions may include program code instructions for receiving a message from a client device, extracting client telemetry data from the message, and enabling reception of the message by the second application with the client telemetry data removed. The message may include client telemetry data inserted into a portion of the message at the client device. The message may have been intended to be communicated from a first application of the client device to a second application (e.g., of a server device) via a network in association with inter-application communication that is otherwise unrelated to client telemetry data.

In another exemplary embodiment, an apparatus for providing in-band client telemetry data is provided. The apparatus may include processing circuitry. The processing circuitry may be configured for receiving a message from a client device, extracting client telemetry data from the message, and enabling reception of the message by the second application with the client telemetry data removed. The message may include client telemetry data inserted into a portion of the message at the client device. The message may have been intended to be communicated from a first application of the client device to a second application (e.g., of a server device) via a network in association with inter-application communication that is otherwise unrelated to client telemetry data.

BRIEF DESCRIPTION OF THE SEVERAL VIEWS OF THE DRAWING(S)

Having thus described embodiments of the invention in general terms, reference will now be made to the accompanying drawings, which are not necessarily drawn to scale, and wherein:

DETAILED DESCRIPTION

Figure 1:
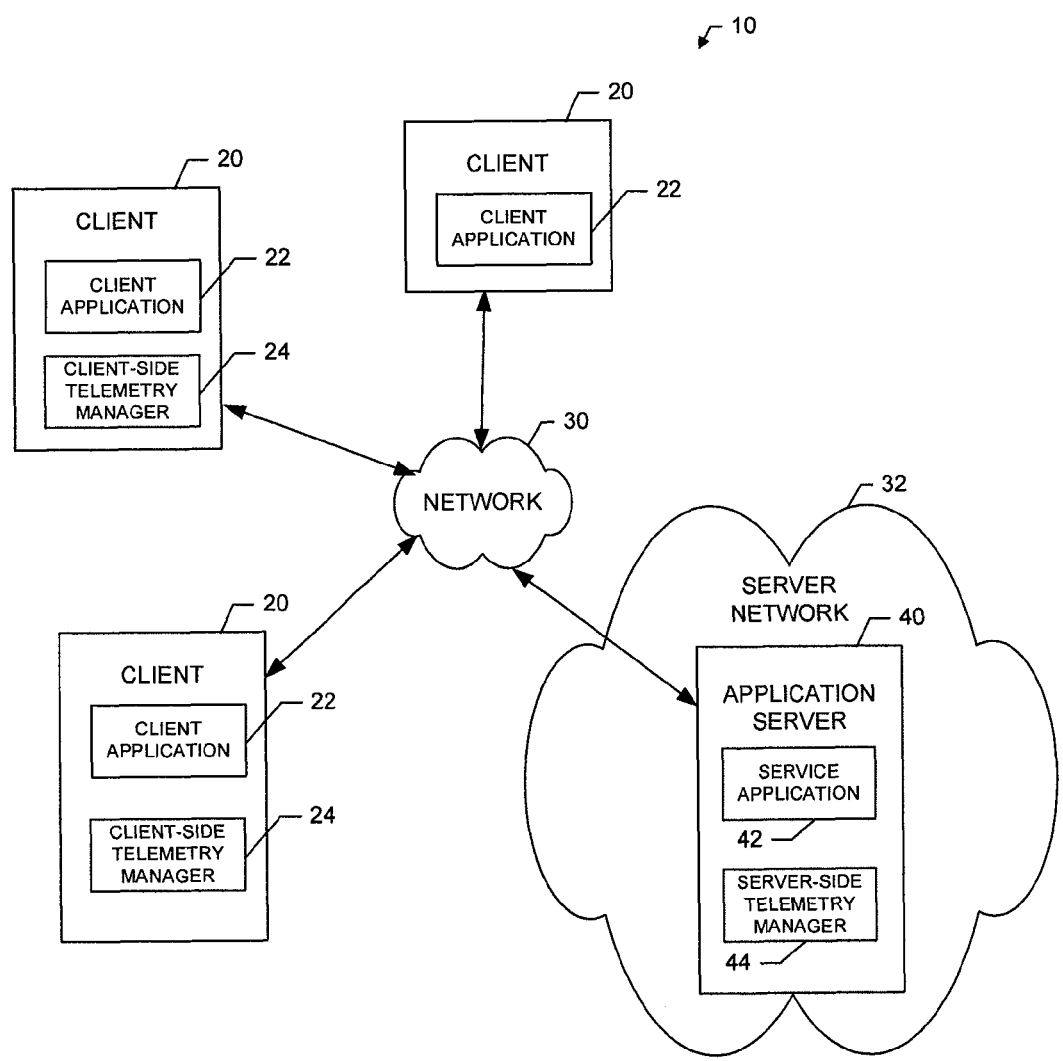
FIG. 1 is a block diagram illustrating a system for providing in-band client telemetry data according to an exemplary embodiment of the present invention.

Embodiments of the present invention will now be described more fully hereinafter with reference to the accompanying drawings, in which some, but not all embodiments of the invention are shown. Indeed, embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As indicated above, embodiments of the present invention are aimed at providing a mechanism by which to improve network performance by providing in-band client telemetry data. Conventional networks often employ separate channels or additional messages for the provision of client telemetry data. For example, the server may be enabled to request (via a specific message) telemetry data and the client may be enabled to respond to the request (again with a specific message) providing the requested telemetry data. Such communication of client telemetry data is "out of band" since it requires separate messaging and perhaps additional communication round trips. According to example embodiments, the telemetry data is provided "in-band" due to the fact that such data is provided in the context of normal or standard messages that would already or otherwise be provided even without the practice of embodiments of the present invention. As such, for example, client telemetry data may be piggybacked onto standard client-server communication messages in order to increase the utility of communications without correspondingly increasing either the number of messages or the number of communication round trips.

An example embodiment will now be described in reference to FIG. 1, which illustrates an exemplary system in which an embodiment of the present invention may be employed. As shown in FIG. 1, a system 10 according to an exemplary embodiment may include one or more clients 20 that may, in some cases, be associated with different corresponding units or departments of a hospital or healthcare system. However, in other cases, the clients 20 could actually be associated with entirely different organizations or healthcare systems or even with the computers or access terminals of patients or outside agencies. As such, for example, one client 20 may be associated with a first entity (e.g., a particular treatment unit, a particular doctor's office, a patient, a management entity, a hospital wing or department, and/or the like) and a second client 20 may be associated with a second entity (e.g., another one of the entities listed above or some other entity).

Each client 20 may be, for example, a computer (e.g., a personal computer, laptop computer, network access terminal, or the like) or may be another form of computing device (e.g., a personal digital assistant (PDA), cellular phone, or the like) capable of communication with a network 30. As such, for example, each client 20 may include (or otherwise have access to) memory for storing instructions or applications for the performance of various functions and a corresponding processor for executing stored instructions or applications. Each client 20 may also include software and/or corresponding hardware for enabling the performance of the respective functions of the clients as described below. In an exemplary embodiment, one or more of the clients 20 may include a client application 22 configured to execute a particular functionality or set of instructions aimed at accomplishing a particular task or carrying out a particular set of operations. In this regard, for example, the client application 22 may include software for enabling a respective one of the clients 20 to communicate with the network 30 for the provision of and receipt of information associated with providing a desired functionality that is defined by the instructions of the corresponding client application 22. As such, for example, the client application 22 may include corresponding executable instructions for configuring the client 20 to provide corresponding functionalities for the provision of and receipt of information associated with any of a number of possible tasks that may be available locally or via the network 30.

The network 30 may be a data network, such as a local area network (LAN), a metropolitan area network (MAN), a wide area network (WAN) (e.g., the Internet), and/or the like, which may couple the clients 20 to devices such as processing elements (e.g., personal computers, server computers or the like) or databases. Communication between the network 30, the clients 20 and the devices or databases (e.g., servers) to which the clients 20 are coupled may be accomplished by either wireline or wireless communication mechanisms and corresponding protocols. In some embodiments, the network 30 may be a secured network to enable secure transmission of patient information in accordance with privacy standards.

In an exemplary embodiment, devices to which the clients 20 may be coupled via the network 30 may include one or more application servers (e.g., application server 40), which may form respective elements of a server network 32. Although the application server 40 is referred to as a "server", this does not necessarily imply that it is embodied on a single device. As such, for example, a server may include a server bank or multiple servers. Moreover, a server could simply be a computer or other computing device acting in a server capacity with respect to the provision of a service to another device (e.g., the client 20) without being a blade server including rack units and/or the like. The application server 40 may include hardware and/or software for configuring the application server 40 to perform various functions. As such, for example, the application server 40 may include processing logic and memory enabling the application server 40 to access and/or execute stored computer readable instructions for performing various functions. In an exemplary embodiment, one function that may be provided by the application server 40 may be the provision of any of a plurality of services with respect to the clients 20. As such, in various exemplary embodiments, certain operations and functionalities described herein in relation to the provision of in-band client telemetry data may be fully implemented at one device, or may be implemented in a distributed fashion with different activities being shared between the client 20 and the application server 40. In some examples, the application server 40 may include a service application 42 comprising stored instructions for accessing information and providing such information to the client applications 22 based on requests provided at each respective client 20.

Accordingly, it should be appreciated that the clients 20 and the application server 40 may communicate with each other (and perhaps also other devices) according to numerous communication protocols including Hypertext Transfer Protocol (HTTP), HTTP secure (HTTPS) and/or the like, to thereby carry out various communication or other functions of the clients 20 and the application server 40, respectively. In an example embodiment, one or more of the clients 20 may include a client-side telemetry manager 24 for inserting telemetry data into the communications that are otherwise exchanged between the clients 20 and the application server 40. Meanwhile, the application server 40 may include its own instantiation of a server-side telemetry manager 44 for extracting the telemetry data inserted by the telemetry data inserter 24.

Additionally or alternatively, the application server 40 may be configured to manage the clients 20 with respect to their provision of telemetry data to the application server 40, for use by the application server 40 in responding to, managing or monitoring client telemetry data. As such, in an example embodiment, the server-side telemetry manager 44 may be configured to insert management commands directed to the client-side telemetry manager 24 to instruct the client-side telemetry manager 24 with respect to its provision of telemetry data to the application server 40. In these example embodiments, the client-side telemetry manager 24 may also be configured to extract management commands from communications received from the server-side telemetry manager 44.

Figure 2:
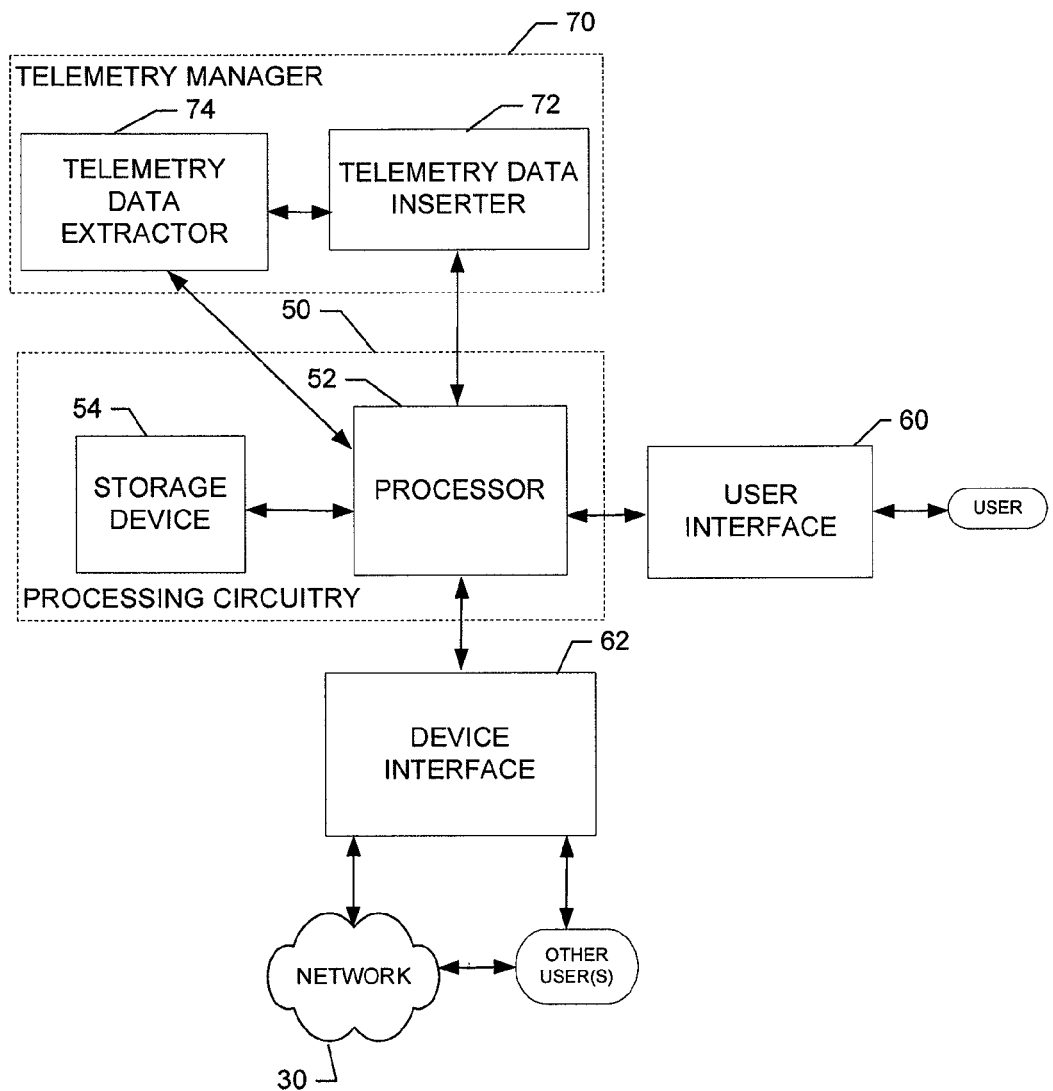
FIG. 2 is a block diagram showing various components that may be included in an apparatus for providing in-band client telemetry data according to an exemplary embodiment of the present invention.

An exemplary embodiment of the invention will now be described with reference to FIG. 2. FIG. 2 shows certain elements of an apparatus for providing in-band client telemetry data according to an exemplary embodiment. The apparatus of FIG. 2 may be employed, for example, on a client (e.g., any of the clients 20 of FIG. 1) or a variety of other devices (such as, for example, a network device, server, proxy, or the like (e.g., the application server 40 of FIG. 1)). Alternatively, embodiments may be employed on a combination of devices. Accordingly, some embodiments of the present invention may be embodied wholly at a single device (e.g., the application server 40 one of the clients 20) or by devices in a client/server relationship (e.g., the application server 40 and one or more clients 20). Furthermore, it should be noted that the devices or elements described below may not be mandatory and thus some may be omitted in certain embodiments.

Referring now to FIG. 2, an apparatus for providing in-band client telemetry data is provided. The apparatus may include or otherwise be in communication with processing circuitry 50 that is configured to perform data processing, application execution and other processing and management services according to an exemplary embodiment of the present invention. In one embodiment, the processing circuitry 50 may include a processor 52, a storage device 54 that may be in communication with or otherwise control a user interface 60 and a device interface 62. As such, the processing circuitry 50 may be embodied as a circuit chip (e.g., an integrated circuit chip) configured (e.g., with hardware, software or a combination of hardware and software) to perform operations described herein. However, in some embodiments, the processing circuitry 50 may be embodied as a portion of a server, computer, laptop, workstation or even one of various mobile computing devices. In situations where the processing circuitry 50 is embodied as a server or at a remotely located computing device, the user interface 60 may be disposed at another device (e.g., at a computer terminal or client device such as one of the clients 22) that may be in communication with the processing circuitry 50 via the device interface 62 and/or a network (e.g., network 30).

The user interface 60 may be in communication with the processing circuitry 50 to receive an indication of a user input at the user interface 60 and/or to provide an audible, visual, mechanical or other output to the user. As such, the user interface 60 may include, for example, a keyboard, a mouse, a joystick, a display, a touch screen, a microphone, a speaker, and/or other input/output mechanisms. In an exemplary embodiment in which the apparatus is embodied as a server (e.g., the application server 40) or some other network devices, the user interface 60 may be limited, or eliminated. However, in an embodiment in which the apparatus is embodied as a client device (e.g., the client 20), the user interface 60 may include, among other devices or elements, any or all of a speaker, a microphone, a display, and a keyboard or the like.

The device interface 62 may include one or more interface mechanisms for enabling communication with other devices and/or networks. In some cases, the device interface 62 may be any means such as a device or circuitry embodied in either hardware, software, or a combination of hardware and software that is configured to receive and/or transmit data from/to a network and/or any other device or module in communication with the processing circuitry 50. In this regard, the device interface 62 may include, for example, an antenna (or multiple antennas) and supporting hardware and/or software for enabling communications with a wireless communication network and/or a communication modem or other hardware/software for supporting communication via cable, digital subscriber line (DSL), universal serial bus (USB), Ethernet or other methods. In situations where the device interface 62 communicates with a network, the network may be any of various examples of wireless or wired communication networks such as, for example, data networks like a Local Area Network (LAN), a Metropolitan Area Network (MAN), and/or a Wide Area Network (WAN), such as the Internet.

In an exemplary embodiment, the storage device 54 may include one or more non-transitory memory devices such as, for example, volatile and/or non-volatile memory that may be either fixed or removable. The storage device 54 may be configured to store information, data, applications, instructions or the like for enabling the apparatus to carry out various functions in accordance with exemplary embodiments of the present invention. For example, the storage device 54 could be configured to buffer input data for processing by the processor 52. Additionally or alternatively, the storage device 54 could be configured to store instructions for execution by the processor 52. As yet another alternative, the storage device 54 may include one of a plurality of databases that may store a variety of files, contents or data sets. Among the contents of the storage device 54, applications (e.g., client application 22 or service application 42) may be stored for execution by the processor 52 in order to carry out the functionality associated with each respective application.

The processor 52 may be embodied in a number of different ways. For example, the processor 52 may be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. In an exemplary embodiment, the processor 52 may be configured to execute instructions stored in the storage device 54 or otherwise accessible to the processor 52. As such, whether configured by hardware or software methods, or by a combination thereof, the processor 52 may represent an entity (e.g., physically embodied in circuitry) capable of performing operations according to embodiments of the present invention while configured accordingly. Thus, for example, when the processor 52 is embodied as an ASIC, FPGA or the like, the processor 52 may be specifically configured hardware for conducting the operations described herein. Alternatively, as another example, when the processor 52 is embodied as an executor of software instructions, the instructions may specifically configure the processor 52 to perform the operations described herein.

In an exemplary embodiment, the processor 52 (or the processing circuitry 50) may be embodied as, include or otherwise control a telemetry manager 70 (e.g., the client-side telemetry manager 24 if the apparatus is instantiated at the client 20 or the server-side telemetry manager 44 if the apparatus is instantiated at the application server 40). In some embodiments, the telemetry manager 70 may further include a telemetry data inserter 72 and/or a telemetry data extractor 74. The telemetry manager 70, the telemetry data inserter 72, and the telemetry data extractor 74 may each be any means such as a device or circuitry operating in accordance with software or otherwise embodied in hardware or a combination of hardware and software (e.g., processor 52 operating under software control, the processor 52 embodied as an ASIC or FPGA specifically configured to perform the operations described herein, or a combination thereof) thereby configuring the device or circuitry to perform the corresponding functions of the telemetry manager 70, the telemetry data inserter 72, and the telemetry data extractor 74, respectively, as described below.

By employing the telemetry manager 70, embodiments of the present invention may enable determinations to be made at the server side as to performance issues that may be experienced at the client side. In this regard, client telemetry data that is indicative of status and performance characteristics measurable or otherwise determinable at the client side. In some examples, client telemetry data may include system performance data, device status, resource utilization statistics, user behavior, and/or the like. The telemetry manager 70 at the client-side (e.g., the client-side telemetry manager 24) may be configured to collect (or initiate collection of) selected telemetry data for provision to the server-side (e.g., the server side telemetry manager 44) for use in connection with, for example, adjusting service provision to the client 20 based on the telemetry data. As such, in some embodiments, the telemetry manager 70 may include or otherwise communicate with sensors and/or devices or applications configured to monitor specific parameters related to client telemetry data.

The telemetry data inserter 72 may be configured to insert or weave client telemetry data into standard messages sent between the client 20 and the application server 40. On the client-side, the telemetry data inserter 72 may insert client telemetry data that has been collected into messages of any communication protocol. In some embodiments, the telemetry data inserter 72 may intercept message traffic intended to be communicated from the client 20 to the application server 40 (e.g., in the case of the client-side telemetry manager 24). In an example embodiment, the weaving of telemetry data may be accomplished by adding the telemetry data to one or more portions of the message traffic. For example, telemetry data could be added to the end, the beginning or be punctured into one or more locations within the payload of the message traffic. In some cases, the telemetry data may be inserted into a header of the message traffic. In an example embodiment, the message traffic may further include an identifier to indicate (e.g., to the telemetry data extractor 74) whether telemetry data is inserted in a particular message and perhaps also the location of the telemetry data. As an example, the identifier may indicate that no telemetry data is included or may indicate that telemetry data is included in the message. In some situations where telemetry data is included, the identifier may further include information indicative of the location of the telemetry data. The information indicative of location may include an indication of the start of the telemetry data and the length thereof or an express indication of both the start and stop locations of the telemetry data.

The telemetry data extractor 74 may be configured to extract telemetry data from incoming message traffic. In many situations, it may be desirable to limit or even eliminate the awareness of applications such as the client application 22 and the service application 42 regarding the operation of the telemetry manager 70. Thus, for example, communications between the client application 22 and the service application 42 may be intercepted (unknown to the client application 22 and the service application 42) by the telemetry data extractor 74 (and the telemetry data inserter 72) to carry out the operations of example embodiments. Accordingly, in an example embodiment, the telemetry data extractor 74 may be configured to intercept incoming message traffic and parse the message traffic for the identifier indicating the presence (or absence) of telemetry data in the message traffic. If telemetry data is included in a particular message, the telemetry data extractor 74 may be configured to remove the telemetry data for processing. The removal of the telemetry data may be guided by the indication as to the location of the telemetry data. Thus, for example, if an indication of the start of the telemetry data and the length thereof or an express indication of both the start and stop locations of the telemetry data is included, only the corresponding data may be removed from the message traffic before the remainder of the message traffic is passed on to the application for which it was sent. Thus, operation of the telemetry manager 70 may be transparent to the client application 22 and the service application 42.

In an example embodiment, the telemetry manager 70, having received the extracted telemetry data, may process the extracted telemetry data so that network operations (e.g., application server 40 or other network device operating parameters) may be altered or otherwise managed based on the telemetry data. Moreover, since the telemetry data is extracted prior to the message traffic being provided to the corresponding application with which the message traffic is associated, there may be no impact on application-specific code.

For the general description provided above, it may be evident that some embodiments of the present invention may include a telemetry manager 70 that is different based on whether it operates at the client-side or server-side. For example, in some embodiments, the client-side telemetry manager 24 only may include the telemetry data inserter 72 while the server-side telemetry manager 44 only may include the telemetry data extractor 74. Thus, telemetry data may be provided from the client 20 to the application server 40 without increasing communication overhead by increasing the number of messages. However, some alternative embodiments may be implemented in which both the telemetry data inserter 72 and the telemetry data extractor 74 are instituted at each of the client-side telemetry manager 24 and the server-side telemetry manager 44. In such examples, the telemetry data inserter 72 on the server-side may be configured to insert management commands into messages bound for the client 20 and the telemetry data extractor 74 of the client-side may be configured to extract the management commands from incoming messages. In an example embodiment, management commands may be weaved into message traffic after such message traffic has been intercepted on its way from the server-side to the client-side. Similarly, the message traffic received at the client side may be intercepted so that the management commands may be extracted prior to the message traffic (restored after extraction of the management commands) being processed normally at the client-side. Management commands may be used to specify turning telemetry reporting on or off, defining reporting intervals for reporting of telemetry data, defining specific parameters (or types of data) to be reported in telemetry data, defining specific times or events in response to which reports are to be provided, requesting an increase or decrease in reporting frequency, and/or the like. When the client-side telemetry manager 24 receives management commands, the client-side telemetry manager 24 may adjust the collection of telemetry data and the reporting thereof based on the management commands.

Accordingly, embodiments of the present invention may provide a flexible (e.g., by the ability to use management commands) mechanism by which client telemetry data may be provided in-band to avoid increases to message latency due to an increase in the number of messages that must be processed. Based on the client telemetry data, performance issues may be diagnosed and corrected. Moreover, in some cases, performance issues may be predicted prior to their inception so that performance reductions can be avoided or mitigated. Overall system performance may therefore be enhanced.

Figure 3:
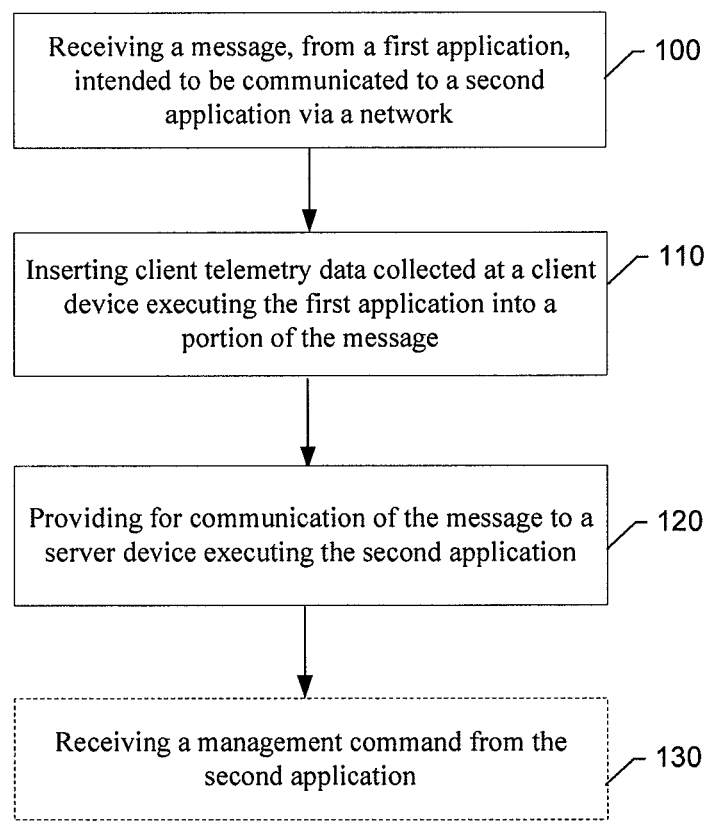
FIG. 3 is a block diagram according to an exemplary method for providing in-band client telemetry data according to an exemplary embodiment of the present invention.
Figure 4:
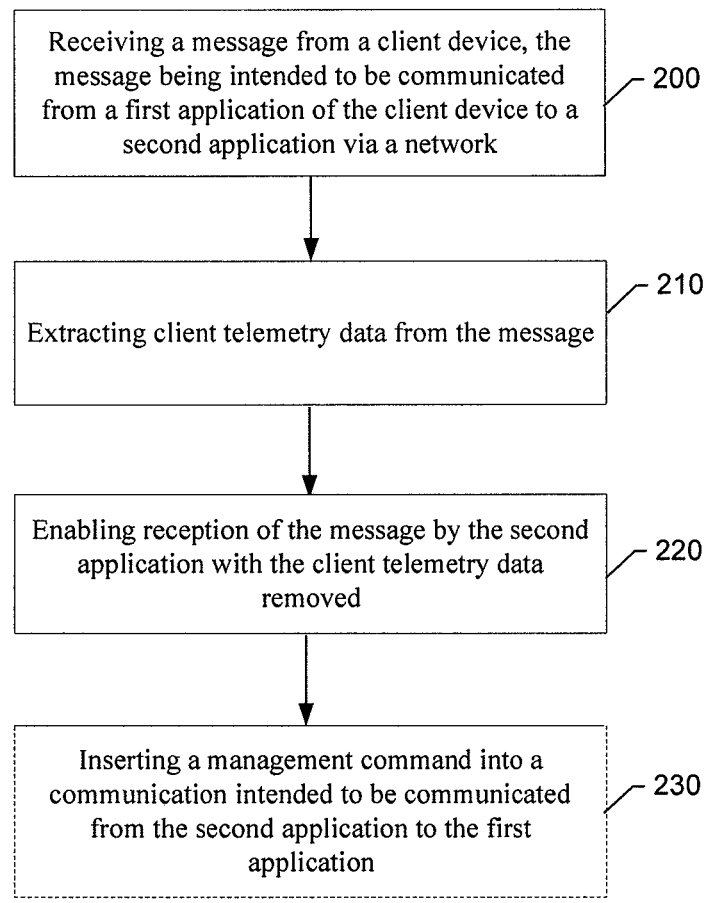
FIG. 4 is a block diagram according to an alternative exemplary method for providing in-band client telemetry data according to an exemplary embodiment of the present invention.

Embodiments of the present invention may therefore be practiced using an apparatus such as the one depicted in FIG. 2. However, other embodiments may be practiced in connection with a computer program product for performing embodiments of the present invention. FIGS. 3 and 4 are flowcharts of a method and program product according to exemplary embodiments of the invention. Each block of the flowcharts of FIGS. 3 and 4, and combinations of blocks in the flowcharts, may be implemented by various means, such as hardware, firmware, processor, circuitry and/or another device associated with execution of software including one or more computer program instructions. Thus, for example, one or more of the procedures described above may be embodied by computer program instructions, which may embody the procedures described above and may be stored by a storage device (e.g., storage device 54) and executed by processing circuitry (e.g., processor 52).

As will be appreciated, any such stored computer program instructions may be loaded onto a computer or other programmable apparatus (i.e., hardware) to produce a machine, such that the instructions which execute on the computer or other programmable apparatus implement the functions specified in the flowcharts block(s). These computer program instructions may also be stored in a non-transitory computer-readable medium comprising memory that may direct a computer or other programmable apparatus to function in a particular manner, such that the instructions stored in the computer-readable memory produce an article of manufacture including instructions to implement the function specified in the flowcharts block(s). The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowcharts block(s).

In this regard, a method according to one embodiment of the invention from the client-side perspective, as shown in FIG. 3, may include receiving a message, from a first application, intended to be communicated to a second application via a network, the message being otherwise unrelated to client telemetry data at operation 100. The message being otherwise unrelated to client telemetry data implies that the message is not a message sent for the purpose of requesting client telemetry data or responding to such a request. Instead, the message is being communicated in the normal course of inter-application (e.g., client and server applications) communication for the performance of some function not directly associated with client telemetry reporting. Thus, were it not for the insertion of the client telemetry data according to an exemplary embodiment, the message would still be sent and would have no direct connection to requesting or reporting of client telemetry data. The method may further include inserting client telemetry data collected at a client device executing the first application into a portion of the message at operation 110 and providing for communication of the message to a server device executing the second application at operation 120.

The message being otherwise unrelated to client telemetry data implies that the message is not a message sent for the purpose of requesting client telemetry data or responding to such a request. Instead, the message is being communicated in the normal course of inter-application (e.g., client and server applications) communication for the performance of some function not directly associated with client telemetry reporting. Thus, were it not for the insertion of the client telemetry data according to an exemplary embodiment, the message would still be sent and would have no direct connection to requesting or reporting of client telemetry data.

In some cases, the method may include additional optional operations, an example of which is shown in dashed lines in FIG. 3. Additionally, in some cases, some of the operations described herein may be modified. In an exemplary embodiment, the method may further include receiving a management command from the second application at operation 130. Although shown as a fourth operation in FIG. 3, it should be appreciated that operation 130 could be the first, second or third operation instead of the being the fourth operation in some alternative embodiments. The management command may define an activity with respect to reporting of client telemetry data based on which the inserting operation is to be performed. In some embodiments, receiving the management command may include receiving a communication from the server device, the communication being otherwise unrelated to client telemetry data, but into which the management command was inserted at the server device, and extracting the management command from the communication. In an example embodiment, inserting the client telemetry data may include inserting an indication into the message to indicate a presence of the client telemetry data. Alternatively or additionally, inserting the client telemetry data may include inserting an indication into the message to indicate a location of the client telemetry data.

An alternative method according to another embodiment of the invention from the server-side perspective is shown in FIG. 4. The method may include receiving a message from a client device at operation 200. The message may include client telemetry data inserted into a portion of the message at the client device. The message may have been intended to be communicated from a first application of the client device to a second application (e.g., of a server device) via a network in association with inter-application communication that is otherwise unrelated to client telemetry data. Again, the message being otherwise unrelated to client telemetry data implies that the message is not a message sent for the purpose of requesting client telemetry data or responding to such a request. Instead, the message is being communicated in the normal course of inter-application (e.g., client and server applications) communication for the performance of some function not directly associated with client telemetry reporting. Thus, were it not for the insertion of the client telemetry data according to an exemplary embodiment, the message would still be sent and would have no direct connection to requesting or reporting of client telemetry data. The method may further include extracting client telemetry data from the message at operation 210 and enabling reception of the message by the second application with the client telemetry data removed at operation 220.

In some cases, the method may include additional optional operations, an example of which is shown in dashed lines in FIG. 4. Additionally, in some cases, some of the operations described herein may be modified. In an exemplary embodiment, the method may further include inserting a management command into a communication intended to be communicated from the second application to the first application at operation 230. Although shown as a fourth operation in FIG. 4, it should be appreciated that operation 230 could be the first, second or third operation instead of the being the fourth operation in some alternative embodiments. The management command may define an activity with respect to reporting of client telemetry data by the client device. In an example embodiment, receiving the message from the client device may include receiving the message including client telemetry data specified according to the management command. In some embodiments, extracting client telemetry data may include extracting the client telemetry data based on receipt of an indication in the message. The indication may indicate a presence of the client telemetry data in the message. Alternatively or additionally, extracting client telemetry data may include extracting the client telemetry data based on receipt of an indication in the message. The indication may indicate a location of the client telemetry data. Other modifications are also possible.

Many modifications and other embodiments of the inventions set forth herein will come to mind to one skilled in the art to which these inventions pertain having the benefit of the teachings presented in the foregoing descriptions and the associated drawings.

Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method comprising:
   receiving a message, from a first application, intended to be communicated to a second application via a network, the message being otherwise unrelated to client telemetry data;
   inserting client telemetry data collected at a client device executing the first application into a portion of the message, wherein inserting the client telemetry data comprises inserting an indication into the message to indicate a presence of the client telemetry data; and
   providing for communication of the message to a server device executing the second application.

2. The method of claim 1, further comprising receiving a management command from the second application, the management command defining an activity with respect to reporting of client telemetry data based on which the inserting operation is to be performed.

3. The method of claim 2, wherein receiving the management command comprises:
   receiving a communication from the server device, the communication being otherwise unrelated to client telemetry data, but into which the management command was inserted at the server device; and
   extracting the management command from the communication.

4. The method of claim 1, wherein inserting the client telemetry data comprises inserting an indication into the message to indicate a location of the client telemetry data.

5. An apparatus comprising processing circuitry configured to:
   receive a message, from a first application, intended to be communicated to a second application via a network, the message being otherwise unrelated to client telemetry data;
   insert client telemetry data collected at a client device executing the first application into a portion of the message, wherein inserting the client telemetry data comprises inserting an indication into the message to indicate a presence of the client telemetry data; and
   provide for communication of the message to a server device executing the second application.

6. The apparatus of claim 5, wherein the processing circuitry is further configured to receive a management command from the second application, the management command defining an activity with respect to reporting of client telemetry data based on which the inserting operation is to be performed.

7. The apparatus of claim 6, wherein the processing circuitry is configured to receive the management command by:

receiving a communication from the server device, the communication being otherwise unrelated to client telemetry data, but into which the management command was inserted at the server device; and extracting the management command from the communication.

8. The apparatus of claim 5, wherein the processing circuitry is further configured to insert the client telemetry data by inserting an indication into the message to indicate a location of the client telemetry data.

9. A method comprising:

receiving a message from a client device, the message including client telemetry data inserted into a portion of the message at the client device, the message being intended to be communicated from a first application of the client device to a second application via a network in association with inter-application communication that is otherwise unrelated to client telemetry data;

extracting client telemetry data from the message, wherein extracting client telemetry data comprises extracting the client telemetry data based on receipt of an indication in the message indicating a presence of the client telemetry data in the message; and enabling reception of the message by the second application with the client telemetry data removed.

10. The method of claim 9, further comprising inserting a management command into a communication intended to be communicated from the second application to the first application, the management command defining an activity with respect to reporting of client telemetry data by the client device.

11. The method of claim 10, wherein receiving the message from the client device comprises receiving the message including client telemetry data specified according to the management command.

12. The method of claim 9, wherein extracting client telemetry data comprises extracting the client telemetry data based on receipt of an indication in the message, the indication indicating a location of the client telemetry data.

13. An apparatus comprising processing circuitry configured to:

receive a message from a client device, the message including client telemetry data inserted into a portion of the message at the client device, the message being intended to be communicated from a first application of the client device to a second application via a network in association with inter-application communication that is otherwise unrelated to client telemetry data;

extract client telemetry data from the message, wherein extracting client telemetry data comprises extracting the client telemetry data based on receipt of an indication in the message indicating a presence of the client telemetry data in the message; and enable reception of the message by the second application with the client telemetry data removed.

14. The apparatus of claim 13, wherein the processing circuitry is further configured to insert a management command into a communication intended to be communicated from the second application to the first application, the management command defining an activity with respect to reporting of client telemetry data by the client device.

15. The apparatus of claim 14, wherein the processing circuitry is configured to receive the message from the client device by receiving the message including client telemetry data specified according to the management command.

16. The apparatus of claim 13, wherein the processing circuitry is further configured to extract client telemetry data by extracting the client telemetry data based on receipt of an indication in the message, the indication indicating a location of the client telemetry data.

* * * * *